United States Patent [19]

Melillo et al.

[11] 4,252,722
[45] Feb. 24, 1981

[54] PROCESS FOR THE PREPARATION OF 6-HYDROXYMETHYL-2-(β-AMINOETHYL-THIO)-1-CARBADETHIAPEN-2-EM-3-CARBOXYLIC ACID

[75] Inventors: David G. Melillo, Scotch Plains; Kenneth M. Ryan, Clark, both of N.J.

[73] Assignee: Merck & Co., Inc., Rahway, N.J.

[21] Appl. No.: 63,490

[22] Filed: Aug. 8, 1979

Related U.S. Application Data

[63] Continuation-in-part of Ser. No. 953,819, Oct. 23, 1978, abandoned.

[51] Int. Cl.$^3$ .................................. C07D 487/04
[52] U.S. Cl. ................... 260/245.2 T; 204/158 R; 260/326.25; 424/274
[58] Field of Search ................... 260/245.2 T Primary Examiner—Mary C. Lee
Attorney, Agent, or Firm—James A. Arno; Julian S. Levitt

[57] ABSTRACT

Diclosed is a process for preparing the antibiotic 6-hydroxymethyl-2-(β-aminoethylthio)-1-carbadethiapen-2-em-3-carboxylic acid (I)

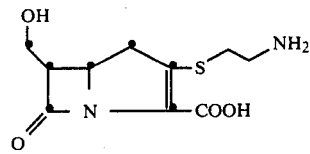

and its pharmaceutically acceptable salt and ester derivatives.

1 Claim, No Drawings

PROCESS FOR THE PREPARATION OF 6-HYDROXYMETHYL-2-(β-AMINOETHYLTHIO)-1-CARBADETHIAPEN-2-EM-3-CARBOXYLIC ACID

BACKGROUND OF THE INVENTION

This application is a continuation-in-part of U.S. Ser. No. 953,819 filed Oct. 23, 1978, now abandoned.

This invention relates to the total synthesis of the antibiotic 6-hydroxymethyl-2-(β-aminoethylthio)-1-carbadethiapen-2-em-3-carboxylic acid (I) and pharmaceutically acceptable salts and esters thereof, which are disclosed and claimed in co-pending, commonly assigned U.S. patent application Ser. No. 933,681 filed Aug. 17, 1978, now abandoned, which application is incorporated herein by reference to the extent that it discloses the utility of I as an antibiotic in animal and human therapy and in inanimate systems.

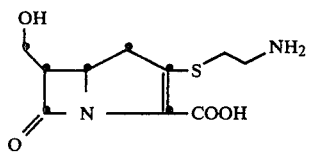

This invention also relates to certain intermediates which are useful in the synthesis of I.

DETAILED DESCRIPTION OF THE INVENTION

The process of the present invention may conveniently be summarized by the following reaction diagram:

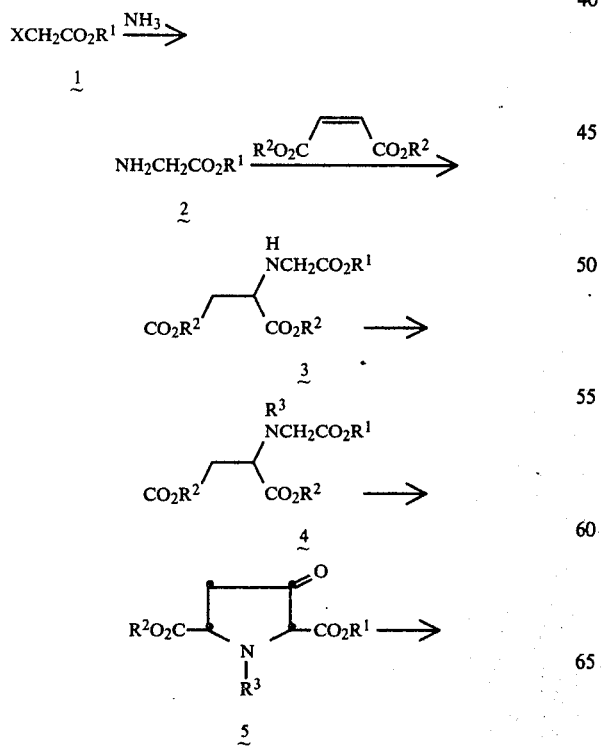

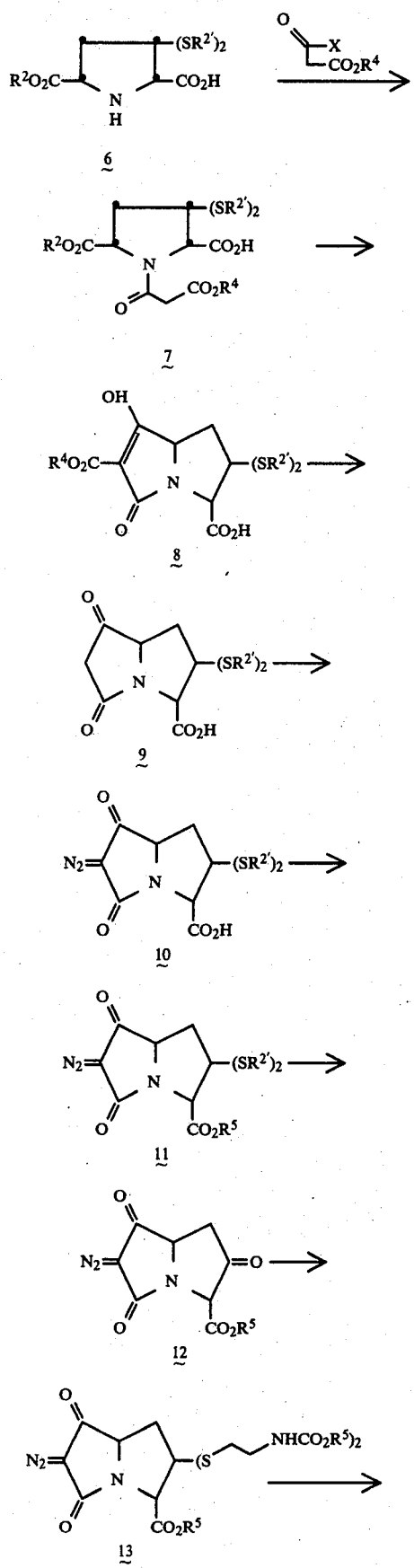

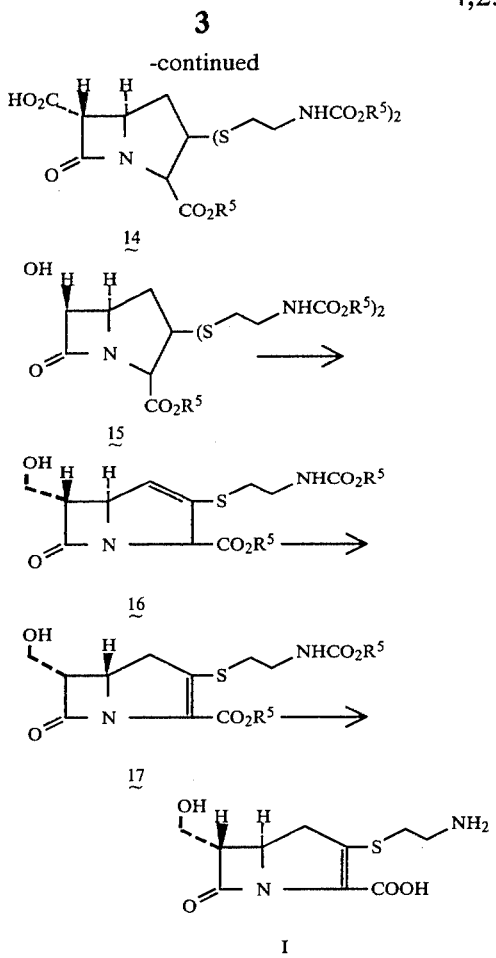

In words relative to the above diagram, the glycine ester 2 is prepared by reacting X-substituted acetate 1 with ammonia. Relative to these intermediates species 1 and 2, $R^1$ is any readily removable carboxyl blocking group such as t-butyl, triphenylmethyl, 2,4-dimethoxybenzyl or the like; and X is a leaving group such as chloro, bromo, iodo, or the like. Typically the reaction 1→2 is conducted by introducing liquid ammonia to 1 in a sealed vessel at a temperature of from −30° C. to 100° C. for from 1 to 24 hours to provide 2. Equivalently, the reaction may be conducted at atmospheric pressure at −33° C. (i.e., refluxing solution of liquid ammonia) for 1-24 hours.

The reaction 2→3 is accomplished by treating 2 with a maleate diester in a solvent such as ethylacetate, aromatic solvents such as toluene, halogenated alkyls such as $CH_2Cl_2$, ether, or the like at a temperature of from 0° C. to 120° C. for from ½ to 24 hours. The ester moieties, $R^2$, which define the maleate diester may be selected from any convenient carboxyl blocking group such as methyl, ethyl, benzyl, or the like. p The aspartic acid intermediate 3 is N-protected according to the reaction 3→4. $R^3$ is any convenient N-protecting group such as carbobenzyloxy, carbo-t-butyloxy, carbomethoxy, or the like; and establishment of $R^3$ is accomplished by reacting the corresponding chloroformate or the like with 3 in an aqueous solvent system at a pH of from 8 to 14 at a temperature of from 0° C. to 100° C. for from ½ to 10 hours. Equivalently a nonaqueous system may be used, e.g., $CH_2Cl_2$, ether, toluene, EtOAc, or the like with, in either class of solvent, from 1 to 10 molar excess of added base (e.g., trialkylamines, $NaHCO_3$, $Na_2CO_3$, NaOH, or the like) to trap the HCl generated during the reaction. Suitable reagents for the establishment of $R^3$ are: benzylchloroformate, methylchloroformate, di-t-butyldicarbonate and the like.

The cyclization of 4 to form pyrrolidinone 5 is accomplished by treating 4 in a solvent such as THF diethyl ether, 1,2-dimethoxyethane, methanol, or the like with a strong base such as sodium methoxide, sodium hydride, or the like at a temperature of from −60° C. to 80° C. for from ¼ to 10 hours.

Thioketal intermediate species 6 is prepared from 5 by treating 5 with $R^{2'}SH$ in a solvent such as methylene chloride, toluene, acetic acid, diethylether, EtOAc or the like in the presence of boron trifluoride etherate ($BF_3.OEt_2$), HBr, trifluoroacetic acid, or the like at a temperature of from 0° C. to 100° C. for from ½ to 10 hours. The mercaptan reagent $R^{2'}SH$ is such that $R^{2'}$ may be alkyl such as methyl, ethyl, isopropyl, or the like, aralkyl such as benzyl, or aryl such as phenyl.

The reaction 6→7 is accomplished by treating 6 in the presence of a base such as triethylamine, sodium bicarbonate, magnesium oxide, sodium carbonate, NaOH, or the like in a solvent such as $CH_2Cl_2$, toluene, ethylacetate, diethylether, or the like with esterified malonyl halide wherein X is halogen such as chloro and $R^4$ is any convenient carboxyl blocking group such as ethyl, t-butyl, methyl, isopropyl, benzyl or the like at a temperature of from 0° C. to 100° C. for from ½ to 10 hours. Alternatively 6 can be treated with an alkyl hydrogen malonate and a dehydrating agent, such as N,N'-dicyclohexylcarbodiimide.

Cyclization of 7 to yield 8 is accomplished by treating 7 in a solvent such as methanol, t-butanol, diethylether, 1,2-dimethoxyethane, tetrahydrofuran or the like with a strong base such as potassium t-butoxide, sodium methoxide, sodium hydride or the like at a temperature of from 0° C. to 100° C. for from 1 to 48 hours.

The reaction 8→9 is accomplished by heating 8 in an aqueous acid solution (for example 1 to 12 NHCl) at a temperature of from 0° C. to 100° C. for from ½ to 24 hours.

The diazotization reaction 9→10 is accomplished by treating 9 in a solvent such as acetonitrile, $CH_2Cl_2$, ether, EtOAc, toluene, dimethylformamide or the like at a temperature of from −50° C. to 60° C. with an azide such as p-toluene sulfonyl azide, p-carboxyphenyl sulfonyl azide or the like followed by the addition of a base such as triethylamine, 1,4-diazabicyclo[2.2.2]octane, pyridine, or the like for from 0.1 to 10 hours.

The carboxyl protecting group $R^5$ is established by the reaction 10→11. Typically this is accomplished from the acid chloride of 10, which is obtained by treating 10 in a solvent such as methylene chloride or the like, preferably in the presence of a catalytic amount of dimethylformamide, with a chlorinating agent such as oxalyl chloride, thionyl chloride, phosgene or the like for from 1 to 10 hours at a temperature of from 0° C. to 85° C. Reaction of the resulting acid chloride with an alcohol in a solvent such as methylene chloride, ether, ethylacetate, toluene or the like in the presence of a base such as triethylamine, pyridine, N,N-dimethylaniline or the like establishes the desired protecting group $R^5$. Suitable alcohols for this esterification include benzyl alcohol, p-nitrobenzyl, or the like. Alternatively, 10 may be converted to a mixed carbonic anhydride, which is then treated as indicated to establish $R^5$. Stepwise oxidation of 11 provides 12. Typically the thioketal 11 in a solvent such as methylene chloride, toluene, ethylacetate or the like is treated with a stoichiometric amount of an oxidizing agent such as m-chloroperbenzoic acid peracetic acid, sodium periodate or the like at a temperature of from −50° C. to 80° C. for from 1 to 24 hours. The resulting sulfoxide intermediate in a solvent such as acetonitrile $CH_2Cl_2$, $Et_2O$, EtOAc, toluene or the like is treated with a 0.2 to 20 fold excess of a strong aqueous acid such as perchloric, sulfuric, hydrochloric or the like at a temperature of from −10° C. to 80° C. for from 0.1 to 5 hours.

The reaction 12→13 is accomplished by treating ketone 12 in an excess of N-protected aminoethanethiol in the presence of boron trifluoride etherate at a temperature of from 0° C. to 100° C. for from 1 to 120 hours. Suitable β-aminoethanethiol reagents include:

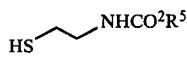

wherein $R^5$ is as defined above and is preferably selected from p-nitrobenzyl, benzyl, 2,4-dimethoxybenzyl and the like.

The ring contraction (13→14) is accomplished by treating 13 in the presence of an equivalent amount of a base such as imidazole, pyridine, triethylamine or the like in a solvent such as methylene chloride, ether, toluene, tetrahydrofuran, ethyl acetate or the like at a temperature of from −100° C. to 60° C. under ultraviolet radiation (250 to 400 nm).

The reaction 14→15 is accomplished by treating 14 in the presence of a reducing agent such as diborane, borane-methylsulfide complex or the like in a solvent such as tetrahydrofuran, 1,2-dimethoxyethane, diethyl ether or the like for from ½ to 10 hours at a temperature of from −50° C. to 85° C.

The reaction 15→16 is accomplished by treating the thioketal 15 in a solvent such as methylene chloride, toluene, ethylacetate or the like in the presence of 1 to 100 mole % water absorbed on the surface of silica gel or alumina (relative to 15) with sulfuryl chloride or the like.

Double bond isomerization 16→17 is accomplished by treating 16 in a solvent such as dimethylsulfoxide, dimethyl formamide, tetrahydrofuran, toluene or the like in the presence of a base such as 1,5-diazabicyclo[5.4.0]undec-5-ene, diisopropylamine or the like at a temperature of from −20° C. to 70° C. for from ¼ to 24 hours.

Final deblocking 17→1 is accomplished by hydrogenolysis in a solvent such as dioxane, ethanol, tetrahydrofuran, or the like or an aqueous mixture thereof in the presence of a platinum metal catalyst such as palladium on charcoal, platinum oxide, or the like under an atmosphere of from 1 to 500 psi hydrogen for from 10 to 300 minutes at 0°−25° C.

Referring again to the reaction diagram, intermediate 5 may be accomplished in a single step according to the following reaction scheme:

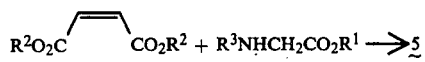

wherein all symbolism has been previously explained.

According to this scheme, the above-defined maleate diester is reacted with a suitably N-protected glycinate ester in the presence of a strong base such as potassium t-butoxide in a solvent such as toluene, diethyl ether, tetrahydrofuran, 1,2-dimethoxyethane or the like at a temperature of from −30° C. to 80° C. for from ¼ to 6 hours; preferably in the presence of excess t-butylacetate. Another variation in the above scheme of total synthesis may be demonstrated at the level of intermediate 13:

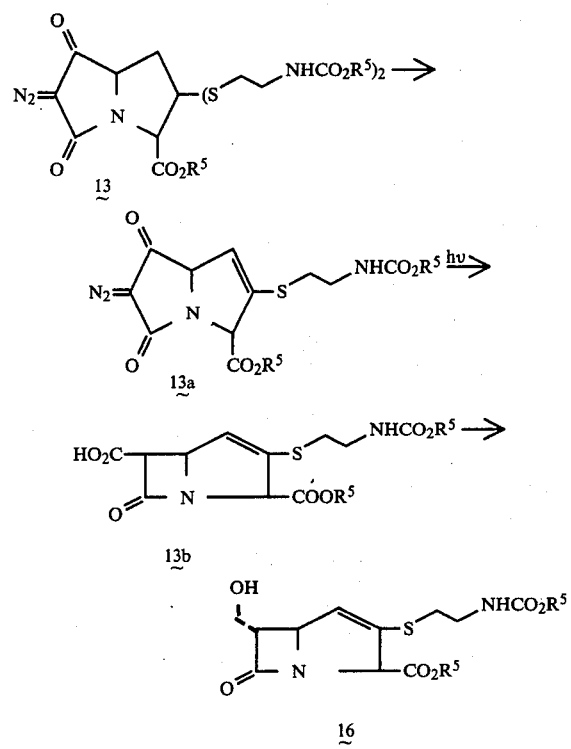

wherein all symbolism has been previously explained; intermediate 16 ties in with the above-detailed scheme of synthesis. In words relative to the above variation, species 13 is converted to 13a on treatment with sulfuryl chloride and wet silica gel in a solvent such as $CH_2Cl_2$, toluene, ethylacetate or the like at a temperature of from −100° C. to 40° C. for from 1 to 60 minutes. Ring contraction according to the above-described procedure for the transformation 13→14 accomplishes the transformation 13a→13b. The transformation 13b→16 is accomplished in a procedure exactly analogous to the above described transformation 15→16.

Another variation in the above described scheme of total synthesis may be explained by the following reaction diagram:

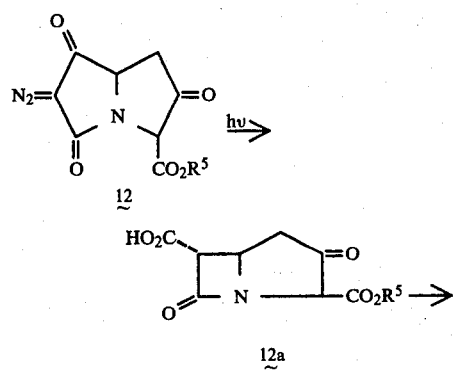

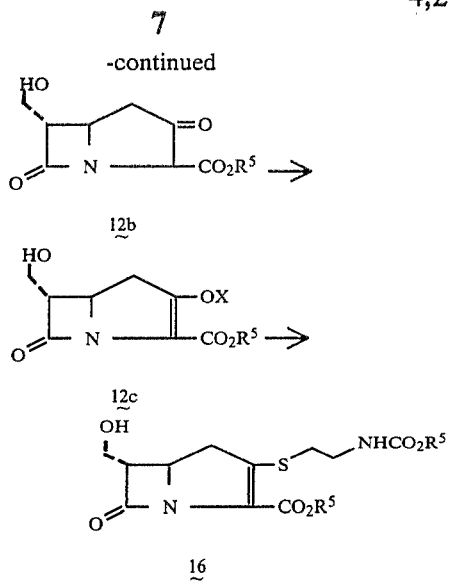

wherein all symbolism has been previously explained. According to this scheme, intermediate 12 (as defined above) is ring contracted by irradiation according to the procedure detailed for the transformation 13→14 above. The resulting species 12a is converted to 12b according to a procedure exactly analoguous to that described for the transformation 14→15, above. The reaction 12b→12c is accomplished by treating 12b in a solvent such as methylene chloride, diethyl ether, toluene, dimethyl formamide or the like with p-toluenesulfonic anhydride, methanesulfonic anhydride, p-toluenesulfonyl chloride, methanesulfonyl chloride and a base such as triethylamine, pyridine or the like at −10° C. to 60° C. for ½ to 5 hours; wherein X is mesyl or tosyl or the like. Establishment of the aminoethylthio side chain is accomplished by treating 12c with N-(carbo-p-nitrobenzyloxy)-2-aminoethanethiol or the like in a solvent such as dimethylformamide, dimethylsulfoxide, hexamethylphosphoramide in the presence of 1 to 2 mole equivalents of a base such as triethylamine, pyridine, or the like, at a temperature of from −10° C. to 50° C. for from ½ to 10 hours. The resulting product 16 is treated as described above in the total synthesis.

The compounds of the present invention (I) are valuable antibiotics active against various gram-positive and gram-negative bacteria and accordingly find utility in human and veterinary medicine. Representative pathogens which are sensitive to antibiotics I include: *Staphyloccus aureus, Escherichia coli, Klebsiella pneumoniae, Bacillus subtilis, Salmonella typhosa, Pseudomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycine; lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydro-phobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to the principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight.

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg. to 1000 mg. In parenteral administration, the unit dosage is usually the pure zwitterionic compound in sterile water solution or in the form of a soluble powder intended for solution.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. All temperatures are in °C.

EXAMPLE 1

Step A

Preparation of Glycine t-butyl ester

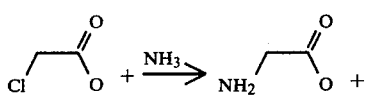

A solution of 150.6 g (1.0 mole) of t-butyl chloroacetate and 300 ml of liquid ammonia is stirred in an autoclave at room temperature (25° C.) for 3 hours. The solution is vented and concentrated. Ethyl ether (300 ml) is added to the residue and filtered. The filtrate is concentrated to give 129.1 g of product as a colorless liquid.

Step B

Preparation of N-(t-butylacetate)aspartic acid dimethyl ester

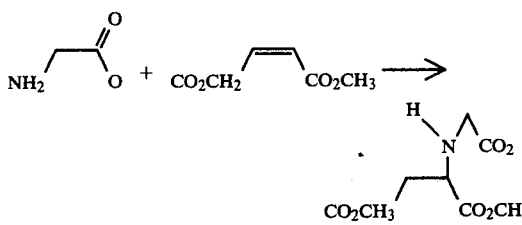

Dimethyl maleate (518 g, 3.92 mole) is added to a solution of 129.1 g (0.98 moles) of glycine t-butyl ester in 1.0 liter chloroform at room temperature. The mixture is stirred at room temperature for 3 hours and then extracted with two 300 ml portions of 2 M aqueous hydrochloric acid. The combined aqueous extracts are basified with sodium hydroxide and the product is extracted with ethyl acetate (600 ml). The organic solution is dried (MgSO₄) and concentrated in vacuo to give 256 g of the product as a colorless oil.

Step C

Preparation of N-(t-butylacetate)-N-(carbobenzyloxy)aspartic acid dimethyl ester

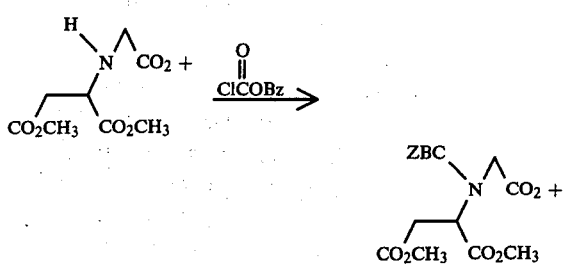

Benzyl chloroformate (165.5 g., 0.97 moles) is added to a mixture of 256 g (0.93 moles) of N-(t-butylacetate)aspartic acid dimethyl ester and 84 g (1 mole) of sodium bicarbonate in 500 ml water. The two-phase solution is stirred at room temperature for 3 hours and then 600 ml EtOAc is added. The organic layer is separated, dried with MgSO₄, and concentrated to an oil. The oil is treated with 1 liter hexane, cooled to 0°, and filtered to give the pure product (365 g) as colorless prisms, m.p. 69°–72°.

Step D

1-Carbobenzyloxy-2-carbo-t-butoxy-5-carbomethoxy-3-pyrrolidinone

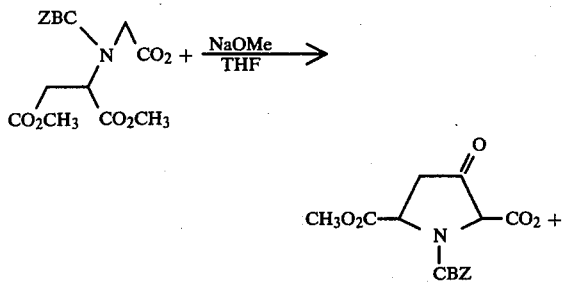

To a cold (0°–5°) suspension of 49.7 g (0.92 moles) of sodium methoxide in 300 ml of tetrahydrofuran (THF) is added a solution of 365 g (0.89 moles) of the aspartate derivative in 500 ml of THF over a period of 15 minutes. After aging at 0°–5° for 15 minutes the reaction mixture is quenched by addition of 70 g of acetic acid. After removing most of the solvent in vacuo, the residue is partitioned between EtOAc and two portions of aqueous sodium carbonate solution. The organic layer is dried over MgSO₄ and concentrated to give 225.0 g of crude pyrrolidinone.

Step E

Preparation of 2-Carboxy-3,3-dithiobenzyl-5-carbomethoxy-pyrrolidine

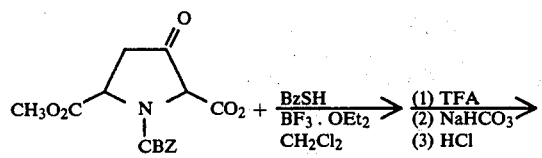

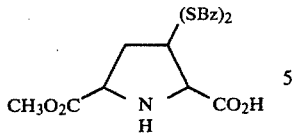

To an ice-cooled solution of 2.0 g. (5.3 mmole) of pyrrolidinone and 2 ml. of benzyl mercaptan in 3 ml. of methylene chloride is added 1.5 ml. of boron trifluoride etherate. The resulting suspension is stirred for 2 hours and then 2.0 ml. of trifluoroacetic acid is added and the suspension warmed to 45° for 3 hours. The yellow solution is cooled to room temperature and excess saturated aqueous sodium bicarbonate is cautiously added. The white solid is collected by filtration, washed with several portions of ethyl acetate, and then partitioned between 2 N aqueous hydrochloric acid and ethyl acetate. The organic phase is washed with water, dried over sodium sulfate and evaporated in vacuo to give 0.84 g of a white foamy solid.

Step F

2-Carboxy-3,3-dithiobenzyl-5-carbomethoxy-1-(ethoxycarbonylacetyl)pyrrolidine

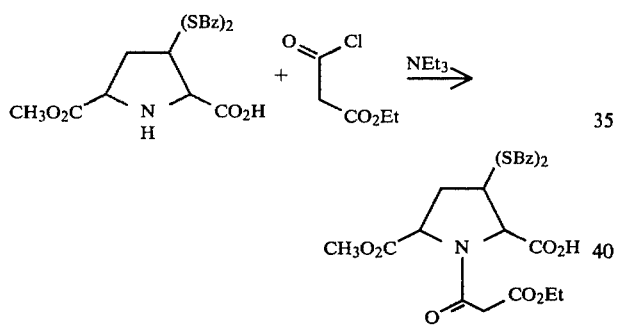

To a solution of the amino acid (140.2 g, 0.336 moles) and 70.7 g (0.70 moles) of triethylamine in 900 ml CH$_2$Cl$_2$ is added a solution of 54.2 g (0.36 moles) of ethylmalonyl chloride in 100 ml CH$_2$Cl$_2$ over a period of 20 min. at room temperature. The resulting mixture is aged at room temperature for 30 min, then washed with two portions of water, dried (MgSO$_4$), and concentrated in vacuo. The oil is dissolved in 800 ml of toluene, cooled to 0° for 3 hrs, and filtered to give 132.5 g of the product as colorless needles.

Step G

2-Carboxy-3,3-dithiobenzyl6,8-dioxo-1-azabicyclo[3.3.0]octane

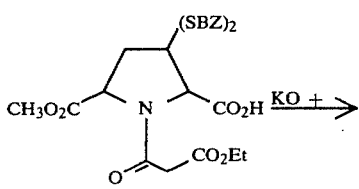

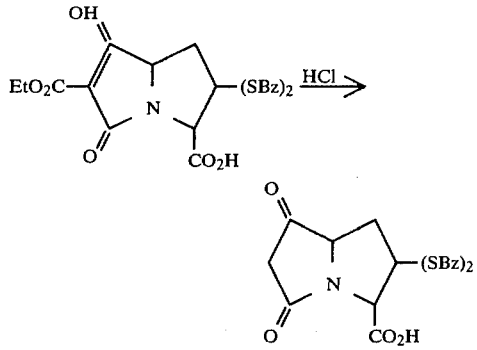

To a solution of the pyrrolidine (151.6 g, 0.29 moles) in 900 ml CH$_3$OH at room temperature is added 67.3 g (0.60 moles) of potassium-t-butyl alcoholate as a solid over 5 minutes. After aging for 24 hrs, the reaction is quenched by adding 42.1 g (0.70 moles) of acetic acid and then concentrated in vacuo. To the residue is added 200 ml of 1 M aq. HCl and 100 ml CH$_2$Cl$_2$ and the resulting solid is collected by filtration to give 144.5 g of the enol ester. The ester is dissolved in 1200 ml acetic acid and 600 ml of 2 N aq. HCl and heated to 75°-80° for 1 hr. The solution is cooled, diluted with H$_2$O, and extracted with two portions (400 ml each) of ethyl acetate. The combined organic layers are dried (MgSO$_4$) and concentrated in vacuo to give 105.3 g of the product as a foamy solid. This material is pure enough to use in Step G.

Step H

2-Carboxy-3,3-dithiobenzyle-7-diazo-6,8-dioxo-1-azabicyclo[3.3.0] octane

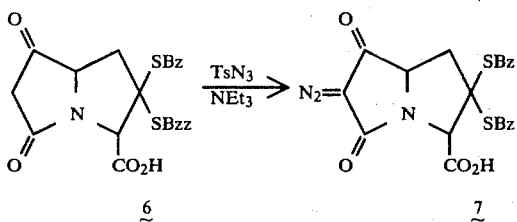

The bicyclic acid (2.96 g, 6.9 mmole) is dissolved in 50 ml of acetonitrile, cooled in an ice-bath, and treated first with a solution of 2.72 g (13.8 mmole) of p-toluenesulfonyl azide in 7 ml acetonitrile and then with a solution of 1.39 g (13.8 mmole) of triethylamine in 7 ml acetonitrile. The resulting brown solution is warmed to room temperature and aged for 40 minutes, then concentrated in vacuo. The residue is dissolved in ethylacetate and washed successively with 2 N-hydrochloric acid, water, and saturated sodium chloride solution. The organic phase is concentrated in vacuo to give 6.8 g of a red liquid which is chromatographed on 140 g of silica gel. After a forerun of 1% acetic acid in methylene chloride is taken, the product is eluted with 1% acetic acid in ethyl acetate. Concentration gives 2.94 g of the product as a yellow-brown solid.

Step I

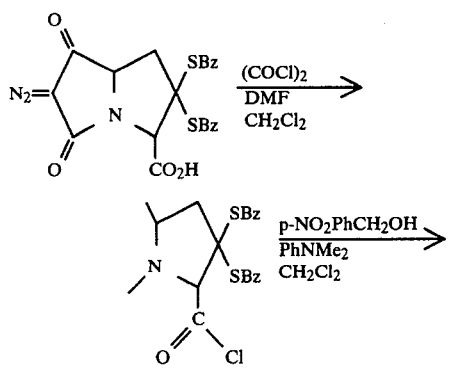

2-Carbo-p-nitrobenzyloxy-3,3-dithiobenzyl-7-diazo-6,8-dioxo-1-azabicyclo[3.3.0]octane To a solution of the acid (2.84 g, 6.27 mmmole) in 20 ml methylene chloride is added 2.10 ml of oxalyl chloride followed by 0.10 ml of N,N-dimethylformamide. The brown solution is aged for 4 hours and then concentrated in vacuo to a brown, oily solid. To an ice-cooled solution of the acid chloride in 16 ml methylene chloride is added a solution of 1.06 g (6.9 mmole) of p-nitrobenzyl alcohol in 3 ml methylene chloride followed by a solution of 0.76 g (6.27 mmole) of N,N-dimethylaniline in 3 ml methylene chloride. The resulting solution is stirred at room temperature for 7 hours and then concentrated. The residue is dissolved in ethylacetate and washed successively with 2 portions of saturated sodium bicarbonate, H$_2$O, 2 portions of 2 N hydrochloride acid and water. The organic phase is dried over MgSO$_4$ and concentrated in vacuo to give 3.1 g of crude ester. Purification is effected by chromatography on 75 g of silica gel. The fractions eluted with 4% ethylacetate in benzene are concentrated to give 2.45 g of ester as a yellow solid. The product can be further purified by recrystallization from 20 ml of diethyl ether to give 2.09 g of yellow prisms, mp=130°-2°.

Step J

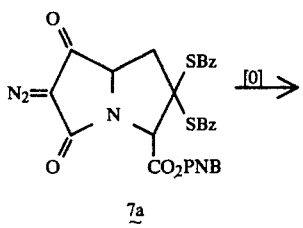

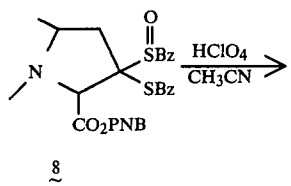

2-Carbo-p-nitrobenzyloxy-7-diazo-3,6,8-trioxoazabicyclo[3.3.0]octane

To an ice-cooled solution of the thioketal (1.62, 2.76 mmole) in 20 ml of methylene chloride is added dropwise a solution of 0.48 g (2.76 mmole) of m-chloroperbenzoic acid in 10 ml of methylene chloride. The resulting solution is aged for 15 minutes and then washed with two portions of saturated sodium bicarbonate and then water. The organic phase is dried of MgSO$_4$, filtered, and concentrated in vacuo to give the crude sulfoxide (mixture of isomers) as a yellow solid. To a solution of the crude sulfoxide in 2.5 ml of acetonitrile is added 0.53 g of a 72% aqueous solution of perchloric acid diluted with 2 ml of acetonitrile. After stirring for 3 minutes the solution is concentrated in vacuo to a yellow oil. The oil is dissolved in ethylacetate and washed with water and then two portions of saturated sodium chloride solution. The organic phase is dried over MgSO$_4$ and concentrated in vacuo to give 1.78 g of a yellow gum. The pure ketone is obtained by crystallization from 50 ml of ethylacetate. The pure product amounts to 0.80 g of yellow prisms m.p.=185 (dec).

Step K

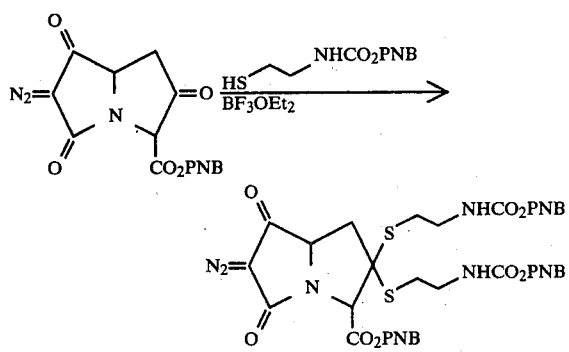

2-Carbo-p-nitrobenzyloxy-3,3-bis(N-carbo-p-nitrobenzyloxy-β-aminoethylthio)-7-diazo-6,8-dioxo-1-azabicyclo[3.3.0]octane A mixture of the ketone (0.23 g, 0.64 mmole) and N-(carbo-p-nitrobenzyloxy)-β-aminoethanethiol (1.82 g, 7.11 mmole) is dissolved in 0.51 ml of boron trifluoride etherate and 10 ml methylene chloride and aged at room temperature for 3 days. The reaction mixture is diluted with ethylacetate and washed successively with water, two portions of 10% lead acetate and solution and water. The organic layer is dried and concentrated in vacuo to give 1.00 g of orange gum. Purification is effected by chromatography on 30 g of silica gel. The fractions eluted with 40% of ethylacetate in toluene are concentrated to give the pure product as a colorless gum (0.38 g).

Step L

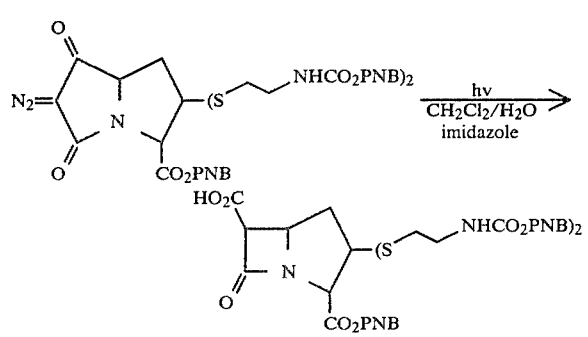

2,2-bis(N-carbo-p-nitrobenzyloxy-β-aminoethylthio)-3-carbo-p-nitrobenzyloxy-1-carbadethiapenam-6-carboxylic acid A solution of the diazo compound (1.65 g, 1.93 mmole) and imidazole (0.13 g, 1.93 mmole) in 35 ml methylene chloride containing 41 mg (2.30 mmole) water is placed in a pyrex vessel fitted with a magnetic stirring bar and a nitrogen inlet tube. The vessel is partially immersed in a dry-ice methanol bath and the solution is thoroughly flushed with nitrogen. The solution is then irradiated for 120 minutes from a distance of 11–15 cm with a 450 watt Hanovia high-pressure mercury vapor lamp fitted with a reflector. The solution is warmed to about 0° and charged on a column of 35 g of silica gel packed in methylene chloride. After a forerun of 25% ethylacetate in benzene, the product is eluted with a mixture of 1% acetic acid and 30% ethyl acetate in methylene chloride. Concentration in vacuo gives the acid (0.68 g) as a pale-yellow gum.

Step M

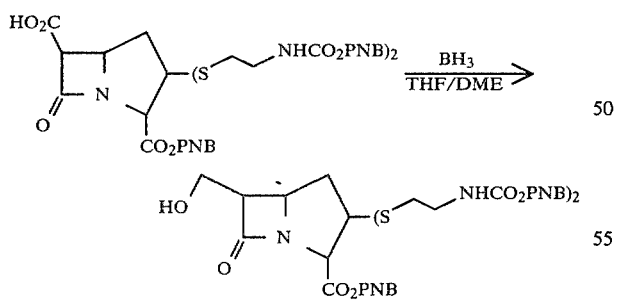

6-hydroxymethyl-2,2-bis(n-carbo-p-nitrobenzyloxy-β-aminoethylthio)-3-carbo-p-nitrobenzyloxy-1-carbadethiapenam A 1 M solution (2.69 ml, 2.69 mmole) of borane in tetrahydrofuran is added dropwise to a solution of the β-lactam acid (1.53 g, 1.81 mmole) in 15 ml of anhydrous 1,2-dimethoxyethane at 0° C. The solution is aged at 0° for 50 minutes and then quenched by addition of 1.5 ml of acetic acid. The solution is diluted with ethylacetate and washed with three portions of water, dried, and concentrated in vacuo to give the crude alcohol as a nearly colorless gum (1.49 g). Chromatography on 30 g of silica gel and concentration of the fractions eluted with 50% ethylacetate in benzene gives the pure alcohol (0.69 g) as a colorless gum.

Step N

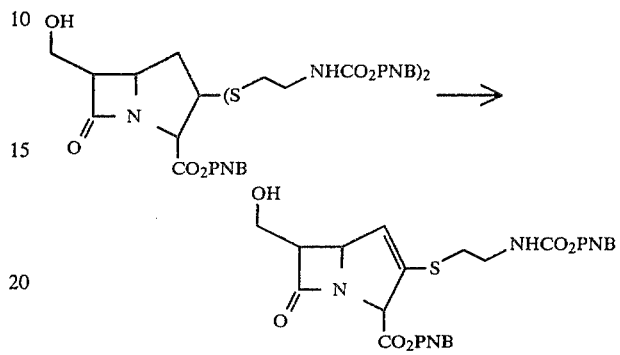

6-hydroxymethyl-2-(N-carbo-p-nitrobenzyloxy-β-aminoethylthio)-3-carbo-p-nitrobenzyloxy-1-carbadethiapen-1-em To a cold (−60°) suspension of the thioketal (0.58 g, 0.70 mmole) and wet silica gel (0.11 g of silica and 0.11 g of water) in 15 ml of methylene chloride is added a solution of sulfuryl chloride (0.11 g, 0.84 mmole) in 1 ml of methylene chloride. The suspension is stirred at −60° for 15 minutes then 5 ml of pH 7.5 aq. phosphate buffer and ethylacetate is added. The organic layer is washed with water, dried and concentrated to give the crude vinyl sulfide. Chromatography on 13 g of silica gel and elution with 45% ethylacetate in benzene gives the pure vinyl sulfide (0.20 g) as a pale yellow gum.

Step O

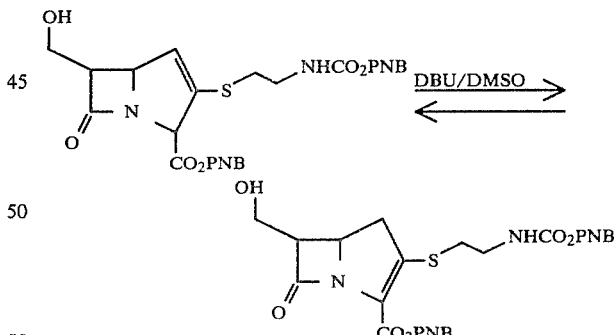

6-hydroxymethyl-2-(N-carbo-p-nitrobenzyloxy-β-aminoethylthio)-3-carbo-p-nitrobenzyloxy-1-carbadethiapen-2-em The vinyl sulfide (0.29 g, 0.51 mmole) is dissolved in 5 ml of dry dimethyl sulfoxide containing 1,5-diazabicyclo[5.4.0]undec-5-ene (0.074 g, 0.49 mmole). The solution is aged at room temperature for 15 minutes and then quenched by addition of 5% aq. potassium dihydrogen phosphate. The product is extracted into ethylacetate, washed with three portions of water, dried and concentrated to give a yellow gum which is chromatographed on 9 g of silica gel. The 45% ethylacetate in benzene fractions are concentrated to give 0.080 g of recovered starting material. The 70% ethyl acetate in benzene fractions afford the pure product (0.081 g) as a yellow gum.

STEP P

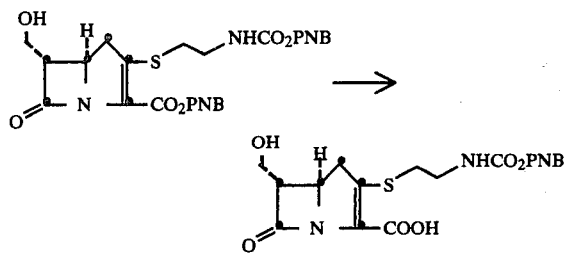

A mixture of vinyl sulfide (0.10 g, 0.17 mmole), and 50 mg of 10% Pd/C, and $K_2HPO_4$ (40 mg, 0.23 mmole) in dioxane (1 ml), ethanol (1 ml), and deionized water (7 ml) is pressurized to 50 psi with hydrogen. The mixture is shaken or stirred at room temperature for 50 minutes and then it is vented and filtered. The catalyst is washed with 2 ml of 0.1 N pH 7 phosphate buffer. The combined filtrates are concentrated in vacuo to the cloud point and then extracted with ethyl acetate. The water layer is concentrated to about 3 ml and charged on a column of 110 g XAD-2 resin. The column is eluted with fractions monitored by UV. Those fractions with UV absorption at 300 m$\mu$ are combined and lyophilized to give the product as a white solid (12.3 mg).

EXAMPLE 2

Step A

1-Carbobenzyloxy-2-carbo-t-butoxy-5-carbomethoxy-3-pyrrolidinone

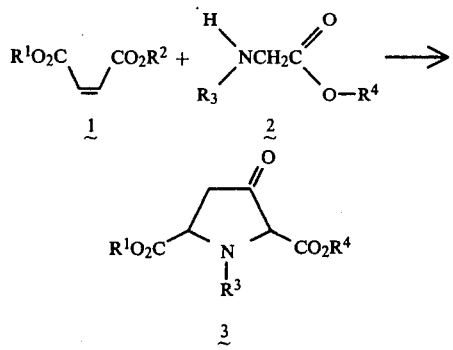

To an ice-cooled suspension of 11.2 g. (0.10 mole) of potassium tert-butyl alcoholate and 125 ml. of dry toluene is rapidly added a mixture of 70 g. (0.60 mole) of t-butyl acetate and 26.5 g. (0.10 mole) of N-carbobenzyloxy-t-butylglycinate. The resulting suspension is aged for 5 minutes and then a solution of 14.4 g. (0.10 mole) of dimethyl maleate is added dropwise. The brown solution is aged at 0° C. for 20 minutes and then quenched by rapid addition of 25 ml. of glacial acetic acid. The organic solution is washed successively with water 2 portions of solid aqueous sodium carbonate and 2 portions of water, then dried ($MgSO_4$) and evaporated in vacuo to give 30.6 g. of viscous, yellow oil.

The crude product is purified by reacting it with 19 g. (0.11 mole) of Girard's Reagent T (carboxymethyl)-trimethylammonium chloride hydrazide) and 12 ml. of glacial acetic acid in 300 ml. of methanol at 55° C. for 2 hours. The solution is concentrated in vacuo. The residue is partitioned between 60 ml. $H_2O$ and 60 ml. ethyl acetate. The aqueous layer is separated, 60 ml. of diethyl ether is added, and 15 ml. of concentrated hydrochloric acid is added with stirring. After 10 min. of stirring, the layers are separated. The organic phase is washed with water, dried ($MgSO_4$) and evaporated in vacuo to give 15.8 g. of pure pyrrolidinone which slowly solidifies on standing.

Step B

2-Carboxy-3,3-dithiomethyl-5-carbomethoxy-pyrrolidine hydrobromide

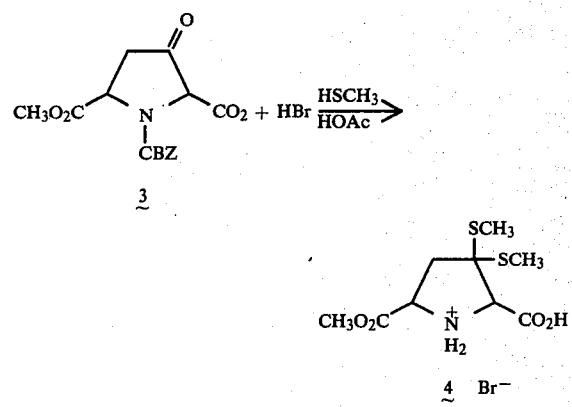

The pyrrolidinone (10.0 g, 0.026 mole) is dissolved in 50 ml. of liquid methyl mercaptan. To this refluxing solution (6°) is added dropwise a solution of 2 g. of hydrogen bromide in 8 ml. of glacial acetic acid. The resulting solution is stirred for 12 hours and then concentrated in vacuo. The oily residue is dissolved in 10 ml. of methanol. With stirring, 400 ml. of ether is added to the methanol solution. The oil which separates is allowed to settle and the solvent is removed by decantation. This dissolution-precipitation procedure is repeated once and then the oil is pumped to constant weight to give 10.78 g of foamy, tan solid.

Step B¹

2-Carboxy-3,3-dithiomethyl-5-carbomethoxy-1-(t-butoxycarbonylacetyl)pyrrolidine

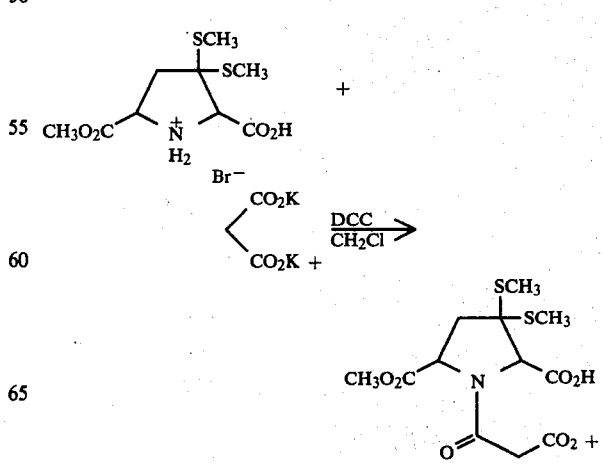

To a stirred suspension of 4.53 g. of amino acid and 2.6 g. of potassium t-butyl malonate in 70 ml. methylene chloride is added a solution of 2.70 g. of N,N'-dicyclohexylcarbodiimide. The suspension is stirred for 20 minutes, then cooled to 0° C. and filtered. The filtrate is washed with 1 N aqueous hydrochloric acid and then the product is extracted into saturated aqueous bicarbonate solution. The basic layer is carefully acidified with 2 N hydrochloric acid and the product extracted into 2 portions of methylene chloride. The combined organic extracts are dried over MgSO and concentrated in vacuo to give 1.48 g. of crude prodduct. Purification is affected by chromatography on 40 g. of silica gel. The product which is contained in the fractions eluted with 1% acetic acid in ethyl acetate amounts to 0.66 g. of colorless oil.

Step C

2-Carboxy-3,3-dithiobenzyl-5-carbomethoxy-1-(t-butoxycarbonylacetyl)pyrrolidine

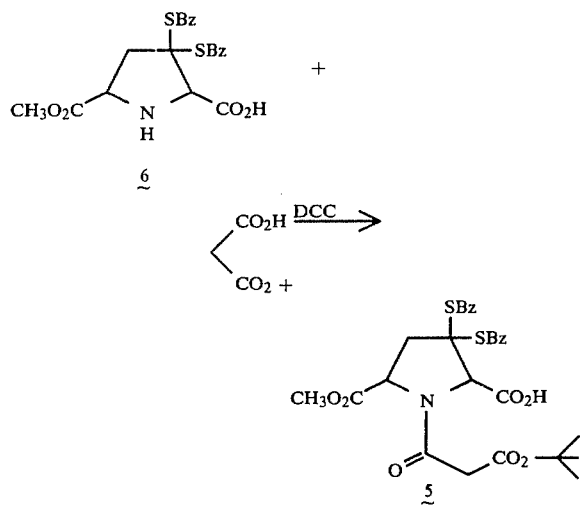

To an ice-cooled solution of 4.17 g. (0.01 mole) of amino acid and 1.6 g. (0.01 mole) of t-butyl hydrogen malonate in 70 ml. of methylene chloride is added a solution of 2.06 g. (0.01 mole) of N,N'-dicyclohexylcarbodiimide in 8 ml. of methylene chloride. The resulting suspension is warmed to room temperature and aged for 2 hours and then filtered. The filtrate is washed with 2 N hydrochloric acid, dried over MgSO4, and concentrated in vacuo to an oil. The crude product is chromatographed on 200 g. of silica gel, after a forerun of 1% acetic acid in methylene chloride the product is eluted with 1% acetic acid in ethyl acetate. Concentration gives the product (mixture of isomers) as a foamy white solid (3.8 g).

Step D

2-Carboxy-3,3-dithiobenzyl-6,8-dioxo-1-azabicyclo[3.3.0]octane

To an ice-cooled solution of the pyrrolidine (5.03 g, 9.0 mmole) in 100 ml of methanol is added 2.02 g (18.0 mmole) of potassium-t-butyl alcoholate. The solution is aged at room temperature for 45 minutes and then heated to reflux for 30 minutes. The solution is concentrated in vacuo. The residue is treated first with 2 N aq. hydrochloric acid and then extracted with three portions of methylene chloride. The combined organic extracts are dried over MgSO4 and concentrated to an orange gum which is dissolved in 100 ml of toluene and refluxed for 2.5 hours. Concentration in vacuo gives 4.2 g of crude product which is purified by chromatography on silica gel (130 g). The product which is eluted with 1% acetic acid in ethyl acetate amounts to 3.96 g of foamy, yellow solid.

EXAMPLE 3

1

Preparation of Pharmaceutical Compositions

One such unit dosage form comprises a blend of 120 mg. of 1 with 20 mg. of lactose and 5 mg. of magnesium stearate which is placed in a No. 3 gelatin capsule. Similarly, by employing more of the active ingredient and less lactose, other dosage forms can be prepared; should it be necessary to mix more than 145 mg. of ingredients together, larger capsules may be employed. Equivalently, compressed tablets and pills can be prepared. The following examples are further illustrative of the preparation of pharmaceutical formulations:

| TABLET | PER TABLET |
| --- | --- |
| Compound 1 | 125 mg. |
| Dicalcium Phosphate | 200 mg. |
| Cornstarch, U.S.P. | 6 mg. |
| Lactose, U.S.P. | 200 mg. |
| Magnesium Stearate | 270 mg. |

The above ingredients are combined and the mixture is compressed into tablets, approximately 0.5 inch in diameter, each weighing 800 mg.

What is claimed is:
1. The compound:

wherein R is hydrogen, a salt cation, or a readily removable protecting group.